United States Patent [19]

Kathawala

[11] 4,185,118

[45] Jan. 22, 1980

[54] BENZOCYCLOALKYLAMIDES

[75] Inventor: Faizulla G. Kathawala, West Orange, N.J.

[73] Assignee: Sandoz, Inc., E. Hanover, N.J.

[21] Appl. No.: 2,974

[22] Filed: Jan. 12, 1979

Related U.S. Application Data

[63] Continuation-in-part of Ser. No. 867,824, Jan. 9, 1978, abandoned.

[30] Foreign Application Priority Data

Dec. 30, 1978 [DE] Fed. Rep. of Germany ....... 2856856

[51] Int. Cl.² .......................... A01N 3/24; C09F 7/00
[52] U.S. Cl. ...................................... 424/324; 260/404
[58] Field of Search ......................... 260/404; 424/324

[56] References Cited

U.S. PATENT DOCUMENTS

| | | | |
|---|---|---|---|
| 3,621,043 | 11/1971 | Seki et al. | 260/404 |
| 3,995,059 | 11/1976 | Fukumara et al. | 424/324 |

*Primary Examiner*—John F. Niebling
*Attorney, Agent, or Firm*—Gerald D. Sharkin; Richard E. Vila; Frederick H. Weinfeldt

[57] ABSTRACT

Unsaturated fatty acid amides of benzocycloalkylamines, eg. N-(1-indanyl)-cis,cis-9,12-octadecadienylamide, are useful as pharmaceutical agents and are obtainable by reacting a mixed anhydride of a long chain unsaturated carboxylic acid with an appropriate benzocycloalkylamine.

18 Claims, No Drawings

BENZOCYCLOALKYLAMIDES

This is a continuation in part of copending application Ser. No. 867,824 filed Jan. 9, 1978, now abandoned.

This invention relates to organic compounds and more particularly to unsaturated fatty acid amides of benzocycloalkylamines, and to pharmaceutical compositions containing such compounds, as well as to the pharmaceutical use of such compounds.

The compounds of this invention are conveniently represented by the formula I:

$$A-\overset{O}{\underset{\|}{C}}-NH-R^1 \qquad I$$

wherein $R^1$ is an benzocycloalkyl nucleus of the structure:

[structure with $(CH_2)_j$, $R^2$, $R^3$]

wherein $R^2$ is a hydrogen atom, halo having an atomic weight of from about 19 to 80, ie. fluoro, chloro or bromo, alkoxy having from 1 to 3 carbon atoms, eg methoxy; or alkyl having from 1 to 3 carbon atoms, eg methyl; and $R^3$ is a hydrogen atom, alkoxy having from 1 to 3 carbon atoms, alkyl having from 1 to 3 carbon atoms, or chloro;

j is a whole integer of from 1 to 4; and

A is the residue of an ethylenically unsaturated long-chain fatty acid minus the carboxylic portion.

It is preferred that when $R^2$ is other than a hydrogen atom, that it be located at a carbon atom ortho to the ring junction; and that when $R^3$ is also other than a hydrogen, it is preferred that it be the same as $R^2$, and it is additionally preferred that it be in para-relationship to $R^2$. It is additionally preferred that the amide group be linked to a carbon of the cycloalkyl moiety which is directly bonded to a ring junction carbon. It is also preferred that j be 1, ie, that the benzocycloalkyl nucleus be indanyl, and particularly 1-indanyl. The A moiety is furnished by long-chain, unsaturated fatty acids having from 8 to 24 carbon atoms and having from 1 to 4 ethylenically unsaturated positions, and include for example oleic, linoleic, linolenic, arachidonic, palmitoleic, vaccenic, and parinaric acids.

Compounds I may be obtained by acylation (process a) of a benzocycloalkylamine of formula II:

$$H_2N-R^1 \qquad II$$

in which $R^1$, is as defined above, with a long-chain, unsaturated fatty acid or derivative thereof corresponding to the moiety -A as defined above. Such "acylation" may be carried out by means conventionally employed in converting an amine function to its corresponding amine, such as are reported in the literature.

The acylation (process a) may conveniently be carried out by a mixed anhydride technique (process a1) wherein a compound II is treated with a mixed anhydride of the formula III:

$$A-\overset{O}{\underset{\|}{C}}-O-\overset{O}{\underset{\|}{C}}-OR^4 \qquad III$$

in which A is as defined above and $R^4$ is a lower unbranched alkyl having from 1 to 6 carbon atoms, at moderate temperatures, eg from about $-10°$ C. to $+35°$ C., in an inert organic medium, eg a chlorinated hydrocarbon, such as methylene chloride.

The mixed anhydrides (III) are obtainable by reacting (process b1) a free carboxylic acid of the formula IV:

$$A-\overset{O}{\underset{\|}{C}}-OH \qquad IV$$

wherein A is as defined above, with a chloroformate of the formula V, $$Cl-\overset{O}{\underset{\|}{C}}-OR^4 \qquad V$$

wherein $R^4$ is as defined above, in the presence of an acid acceptor, eg an organic base, such as triethylamine, at reduced temperatures, eg at from about $-10°$ to $+30°$ C., in an inert organic medium, eg a chlorinated hydrocarbon, such as methylene chloride.

Another convenient method of preparing compounds I comprises reacting (process a2) an acyl halide of the formula VI $$A-\overset{O}{\underset{\|}{C}}-X \qquad VI$$

in which A is as defined above, and X is either chloro- or bromo, with a compound II (as defined above), in the presence of an acid acceptor, in an inert medium at moderate temperatures, eg from about 10° to 50° C. preferably at about 20° to 30° C.

The acyl halides (VI) may be prepared in the conventional manner, eg by treating (process b2) a corresponding compound IV (as defined above), with a halogenating agent capable of contributing a chlorine or bromine atom, eg thionyl chloride (or -bromide, as appropriate).

In the above-described processes, neither the media nor the temperature are critical to the reactions, and where the reactants or reagents are liquid, an excess thereof may serve as the reaction medium. If desired a compound II may be in the form of a water-soluble acid addition salt, for example the hydrochloride. The mixed anhydride (III) resulting from process (b1) may conveniently be used in situ. That is to say that provided that the materials in the reaction mixture containing the mixed anhydride are not detrimental, they may be used directly for process (a1) without recovery.

Embodiments of this invention are Compounds I in which A is of the formula:

$$CH_3-(CH_2)_f(CH=CH)_g(CH_2)_h- \qquad (A1)$$

or $$CH_3-(CH_2)_n(CH=CH-CH_2)_m(CH_2)_p- \qquad (A2)$$

wherein when A is (A1) then
f = 1 to 10, g=1 to 4, and
h=4 to 9, or 3 to 9;
particularly where f=5 or 7, g=1, and h=7; and
when A is (A2) then
n=1 to 4,
m=2 to 4, and
p=2 to 7, or 1 to 7;
particularly where
n=1 or 4, m=from 2 to 4 and p=2 or 6.

The total number of carbon atoms in A1 or A2 conform to the definition of A, above. That is to say that since A is the residue of an acid having from 8 to 24 carbons; A has from 7 to 23 carbons and from 1 to 4 unsaturated positions. Radicals A which are unbranched are preferred. Also generally preferred are the fatty acid derivatives of the natural fatty acid order, ie those in which A represent an odd number of carbon atoms of from 7 to 23 and accordingly A—C=O represent an even number of carbon atoms of from 8 to 24.

Examples of acids suitable to provide A are given in tables I and II below:

Table I

| carbons in A—C=O | A = A1 | | | |
| --- | --- | --- | --- | --- |
|  | f | g | h | acid |
| 16 | 5 | 1 | 7 | palmitoleic |
| 18 | 7 | 1 | 7 | oleic |
| 18 | 10 | 1 | 4 | petroselenoic |
| 18 | 5 | 1 | 9 | vaccenic |
| 18 | 3 | 3 | 7 | punicic (or eleostearic) |
| 18 | 1 | 4 | 7 | parinaric |
| 20 | 9 | 1 | 7 | gadoleic |
| 22 | 9 | 1 | 9 | cetoleic |

Table II

| carbons in A—C=O | A = A2 | | | |
| --- | --- | --- | --- | --- |
|  | n | m | p | acid |
| 18 | 4 | 2 | 6 | linoleic |
| 18 | 1 | 3 | 6 | linolenic |
| 20 | 4 | 4 | 2 | arachidonic |

Those compounds I wherein A is derived from oleic, linoleic, linolenic or arachidonic acids are particularly preferred.

It will be appreciated that the unsaturated acids which provide the moiety A occur in isomeric forms due to the presence of the one or more unsaturated positions. The particular isomeric form of the A moiety in a parent acid will remain the same in the resulting Compound I, since the structural configuration of the A moiety is not changed by the processes yielding compounds I. Compounds I wherein the hydrogen atoms on the pair of carbons of each unsaturated position of the A-moiety are in the cis configuration are preferred.

Particular embodiments of this invention are the compound N-(1-indanyl)-cis-9-octadecenylamide as well as pharmaceutical compositions containing said compound as well as the use of said compound and compositions containing said compound as described herein.

Reagents and reactants described herein, e.g., compounds II, III, IV, V, and VI are known and obtainable by known means, or where not known, may be obtained by adaptation of methods reported in the literature for the preparation of known analogs; many such compounds being commercially available.

The final products and intermediate compounds described herein may be recovered and refined, where such is desired, by conventional means, such as by crystallization, distillation or chromatographic techniques such as column or thin layer chromatography.

STATEMENT OF UTILITY

The compounds of formula I of this invention are useful as pharmaceutical agents in animals. In particular, the compounds of the formula I are useful in controlling the cholesterol ester content of mammalian arterial walls and are therefore particularly indicated for use as antiatherosclerotic agents, ie. agents useful in the prophylactic treatment of atherosclerosis and in the controlling of atherosclerotic conditions due to cholesterol ester accumulation in the arterial walls. Such ability of the compounds of the formula I is indicated by known test procedures in which the total cholesterol ester content of cultured cells is shown to be reduced by a test compound, as compared to untreated cells, and carried out, for example, by the following procedures:

(A) Cell culture

Rhesus monkey smooth muscle cells (from the arterial, eg. aorta, wall) obtained by the method of K. Fisher-Dzoga et al (Experimental and Molecular Pathology 18, 162–176 (1973)) are routinely grown in 75 $cm^2$ tissue culture flasks using Minimum Essential Medium (Eagle) supplemented with 10% fetal bovine serum. For testing a 75 $cm^2$ flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800×g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 800×g, the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 μl of the isopropyl alcoholic solution is added and mixed. After standing at room temperature for approximately 5 minutes, 0.8 ml of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5 N sodium hydroxide solution (Reagent C, Table 1).

Alternatively, the assay for cholesterol, ie Step C (above) obtained from Steps A and B, may be carried out by the method of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

Table 1

| Composition of Reagents for Cholesterol Determination | | |
|---|---|---|
| A. Free Cholesterol Reagent | | |
| Sodium phosphate buffer pH 7.0 | .05 | M |
| Cholesterol oxidase | .08 | U/ml |
| Horseradish peroxidase | 30. | U/ml |
| p-Hydroxyphenylacetic acid | .15 | mg/ml |
| B. Total Cholesterol Reagent | | |
| Sodium phosphate buffer pH 7.0 | .05 | M |
| Cholesterol ester hydrolase | .08 | U/ml |
| Cholesterol oxidase | .08 | U/ml |
| Horseradish peroxidase | 30. | U/ml |
| Sodium taurocholate | 5. | mM |
| Carbowax-6000 | .17 | mM |
| p-Hydroxphenylacetic acid | .15 | mg/ml |
| C. Sodium Hydroxide Solution | .5N | |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams preferably from about 100 milligrams to 2,000 milligrams. Dosage forms suitable for internal use comprise from about 25 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules.

A representative formulation for administration orally three times a day prior to feeding in the treatment of atherosclerosis is a gelatin capsule prepared by conventional techniques to contain the following

| Ingredient | Weight (in Mg.) | |
|---|---|---|
| N-(1-indanyl)-cis-9-octadecenyl-amide | 300 | 300 |
| corn oil | 500 | 200 |

As is the present understanding in the art, controlling th total cholesterol content of an arterial wall by inhibiting the accumulation thereof by reducing the cholesterol ester content thereof, advantageously inhibits the formation of plaques in the arterial wall.

The following examples are illustrative of the invention. All temperatures are centigrade and room temperature is 20° to 30° C., unless indicated otherwise.

EXAMPLE 1

N-(1-Indanyl)-cis,cis-9,12-octadecadienamide

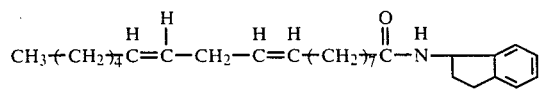

To a solution of 7.0 g linoleic acid in 250 ml methylenechloride cooled to −20° is added 2.5 g triethylamine, and then dropwise 2.7 g ethyl chloroformate. The reaction mixture is allowed to come to room temperature and then stirred 2 hours. To the reaction mixture is then added, dropwise, 3.4 g 1-aminoindan, and the reaction mixture then stirred for 16 hours. The reaction mixture is then extracted several times with 2 N hydrochloric acid, then with 2 N aqueous sodium hydroxide solution, washed well with saturated aqueous sodium chloride, dried over anh. sodium sulphate, filtered and the filtrate evaporated i.v. to dryness. The resulting residue is rapidly filtered over silica gel, with methylene chloride as solvent. The necessary fractions indicated to contain reaction product by thin layer chromatography of samples are pooled and solvent removed by evaporation under vacuum to give title product as a viscous oil, characterized by NMR (in CDCl$_3$); triplet at 5.15 ppm (4 protons) and doublet at 6.4 ppm (1 proton).

EXAMPLE 2

Repeating the procedure of Example 1, but using in place of the linoleic acid used therein, an approximately equivalent amount of:
(a) oleic acid;
(b) linolenic acid;
(c) palmitoleic acid; or
(d) arachidonic acid;
there is accordingly obtained, respectively:
(a) N-(1-indanyl)-cis-9-octadecenylamide;
(b) N-(1-indanyl)-cis, cis, cis-9,12,15-octadecatrienylamide;
(c) N-(1-indanyl)-cis-9-hexadecenylamide; and
(d) N-(1-indanyl)-cis,cis,cis,cis-5,8,11,14-eicosatetraenylamide.

EXAMPLE 3

Repeating the procedure of Example 2a, but using in place of the 1-aminoindan used therein, an approximately equivalent amount of:
(a) 2-aminoindan;
(b) 1-amino-7-methylindan;
(c) 1-amino-7-chloroindan;
(d) 1-amino-4,7-dimethoxyindan; or
(e) 1-amino-1,2,3,4-tetrahydronaphthalene;
there is accordingly obtained, respectively:
(a) N-(2-indanyl)-cis-9-octadecenylamide;
(b) N-[1-(7-methylindanyl)]-cis-octadecenylamide;
(c) N-[1-(7-chloroindanyl)]-cis-octadecenylamide;
(d) N-[1-(4,7-dimethoxyindanyl)]-cis-octadecenylamide; and
(e) N-[1-(1,2,3,4-tetrahydronaphthyl)]-cis-octadecenylamide.

What is claimed is:

1. A compound of the formula:

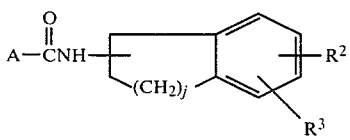

wherein
A is the residue of a fatty acid minus the carboxylic function, and has from 7 to 23 carbon atoms and from 1 to 4 ethylenically unsaturated positions;
$R^2$ is a hydrogen atom, halo having an atomic weight of from about 19 to 80, alkoxy having from 1 to 3 carbon atoms, or alkyl having from 1 to 3 carbon atoms,
$R^3$ is a hydrogen atom, alkoxy having from 1 to 3 carbon atoms, alkyl having from 1 to 3 carbon atoms, or chloro; and
j is a whole integer of from 1 to 4.

2. A compound of claim 1 in which A is of either the types (A1) having the structure:

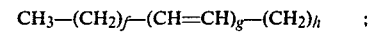

or (A2) having the structure

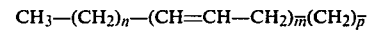

in which f is a whole integer of from 1 to 10, g is a whole integer of from 1 to 4, and h is a whole integer of from 4 to 9; and
n is a whole integer of from 1 to 4,
m is a whole integer of from 2 to 4,
and p is a whole integer of from 2 to 7.

3. A compound of claim 2 in which A is of type (A1).

4. A compound of claim 3 in which A is the residue of oleic acid.

5. A compound of claim 3 in which A is the residue of palmitoleic acid.

6. A compound of claim 2 in which A is of type (A2).

7. A compound of claim 6 in which A is the residue of linoleic acid.

8. A compound of claim 6 in which A is the residue of linolenic acid.

9. A compound of claim 1 of the formula:

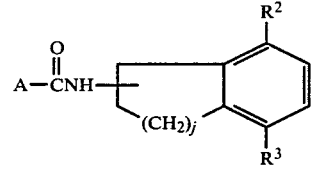

wherein each of A, $R^2$, $R^3$ and j are as defined above.

10. A compound of claim 9 in which $R^2$ is other than a hydrogen atom and $R^3$ is a hydrogen atom.

11. A compound of claim 9 in which both $R^2$ and $R^3$ are other than hydrogen atoms.

12. A compound of claim 1 in which each unsaturated position of A is in the cis- type isomeric form.

13. The compound of claim 7 which is N-(1-indanyl)-cis,cis-9,12-octadecadienamide.

14. The compound of claim 4 which is N-(1-indanyl)-cis-9-octadecenylamide.

15. A method of reducing the cholesterol ester content of an arterial wall, in a mammal in need of such treatment, comprising administering a cholesterol ester-reducing amount of a compound of claim 1 to said mammal.

16. A pharmaceutical composition suitable for reducing the cholesterol ester content of an arterial wall of a mammal comprising a cholesterol ester-reducing effective amount of a compound of claim 1 and a nontoxic pharmaceutically-acceptable carrier.

17. A composition of claim 16 in solid form.

18. A composition of claim 16, in which the compound is present in an amount of from about 25 to 2,500 milligrams.

* * * * *